United States Patent [19]
Zaffaroni

[11] 3,948,254
[45] Apr. 6, 1976

[54] NOVEL DRUG DELIVERY DEVICE

[75] Inventor: Alejandro Zaffaroni, Atherton, Calif.

[73] Assignee: Alza Corporation, Palo Alto, Calif.

[22] Filed: Aug. 28, 1974

[21] Appl. No.: 501,207

Related U.S. Application Data

[63] Continuation-in-part of Ser. No. 198,028, Nov. 8, 1971, abandoned, which is a continuation-in-part of Ser. No. 42,786, June 2, 1970, Pat. No. 3,854,480.

[52] U.S. Cl. ............... 128/127; 128/130; 128/260; 128/271; 3/1; 424/22
[51] Int. Cl.² .................. A61F 5/46; A61M 31/00
[58] Field of Search ............... 128/270–272, 128/127–130, 260; 3/1; 424/22

[56] References Cited
UNITED STATES PATENTS

| | | | |
|---|---|---|---|
| 2,962,023 | 11/1960 | Chappaz et al. ................. | 128/260 |
| 3,757,798 | 9/1973 | Lambert ............................. | 128/260 |
| 3,760,805 | 9/1973 | Higuchi .............................. | 128/130 |
| 3,845,770 | 11/1974 | Theeuwes et al. ................. | 128/130 |
| 3,880,991 | 4/1975 | Yolles ................................ | 128/130 |
| 3,888,975 | 6/1975 | Ramwell ............................ | 128/130 |

*Primary Examiner*—Lawrence W. Trapp
*Attorney, Agent, or Firm*—Paul L. Sabatine; Edward L. Mandell; Thomas E. Ciotti

[57] ABSTRACT

A drug delivery device for administering a drug at a controlled rate for a prolonged period of time to produce a local or systemic physiological or pharmacological effect is comprised of a wall surrounding a reservoir containing a drug. The reservoir is formed of a solid drug carrier permeable to the passage of the drug. The wall is formed in at least a part of a microporous material the pores of which contain a drug release rate controlling medium also permeable to the passage of the drug, but the rate of passage of the drug through the medium is lower than the rate passage of the drug through the solid drug carrier so that drug release by the medium in the microporous wall is the drug release rate controlling step for releasing drug from the drug delivery device.

34 Claims, 8 Drawing Figures

NOVEL DRUG DELIVERY DEVICE

CROSS-REFERENCE TO RELATED APPLICATION

This application is a continuation-in-part of abandoned patent application U.S. Ser. No. 198,028 filed on Nov. 8, 1971, which is a continuation-in-part of copending patent application U.S. Ser. No. 42,786 filed on June 2, 1970 and now U.S. Pat. No. 3,854,480.

BACKGROUND OF THE INVENTION

This invention relates to a novel and useful drug delivery device for releasing drug at a controlled rate for a prolonged period of time to produce a local or systemic physiological or pharmacological effect. The drug delivery device is comprised of a reservoir surrounded by a wall. The reservoir is comprised of a drug within a solid carrier permeable to the passage of the drug and in which the drug has limited solubility. The wall of the device is comprised in at least a part of a microporous material, the pores of which contain a drug release rate controlling medium permeable to the passage of the drug. Both the solid drug carrier and the medium present in the pores of the microporous wall are permeable to the passage of drug, as by diffusion, but the permeability of the medium to the drug is lower than the permeability of the solid carrier to the drug. Accordingly, drug released through the medium in the pores of the wall is the drug release rate controlling step for releasing drug from the drug delivery device of the invention.

The terms and phrases such as "reservoir", "carrier", "drug", "limited solubility", "medium", and the like that appear throughout the specification and the accompanying claims are defined in the specification in the section entitled, "Detailed Description of the Invention."

In many therapeutic programs pertaining to the management of health and disease, it is desirable and indicated to use a drug delivery device to provide for the slow release of a drug to the body at a controlled rate over a prolonged period of time to achieve a desired physiologic or pharmacologic effect. In many instances, such a rate of release of the drug from a drug delivery device should have a zero order time dependence, that is, the rate of drug release is independent of time.

Different approaches have been tried by the prior art to obtain such a drug delivery device. One approach, which has received great attention, is to mix a drug with a carrier material that is gradually broken down by body fluids with the drug released as the carrier disintegrates. Numerous carriers have been used in such devices including waxes, oils, fats, soluble polymers, and the like. While some of these devices have provided for a delayed release of the drug, the desired constant release rate for a prolonged period has not been obtained. One reason for this is that as the carrier disintegrates the surface area of the dosage unit decreases, concomitantly exposing increasingly smaller quantities of the carrier to the surrounding body fluids. This inherently results in a decline in the release rate over time.

Another approach to this problem has been to disperse the drug throughout a solid matrix material through which the desired amount of the drug is released by diffusion. But, this type of drug delivery device has proven incapable of providing a zero order drug release rate, because of the drawback that the release rate ($dM_t/dt$) instead of being zero order ($dM_t/dt$ = constant) decreases with time ($dM_t/dt$ = constant $x\ t^{-\frac{1}{2}}$) during much of the drug release history; J. Pharm. Sci., Vol. 52, pages 1145 to 1149, 1963.

Still another approach has been to enclose the drug within a single capsule having a polymeric wall or walls through which the drug can pass, for example, by diffusion. An approach of this kind is set forth in U.S. Pat. No. 3,279,996. These devices too, have inherent difficulties. One difficulty encountered is that small devices containing a small amount of dry, powdered drug are hard to fabricate because the device can be manufactured from only a few, critical materials and further because these selected materials containing the drug must be non-toxic as they contact the body. Additionally, these prior art devices have generally been based on the use of a single material, such as silicone rubber polymers, especially polydimethylsiloxane, as the diffusion control membrane. In large part, these polymers were selected because of their permeability to some important drug molecules. But, it has been found that mere high permeability without consideration of release rate controlling properties can be a significant disadvantage which defeats the primary object of an acceptable drug delivery device. Thus, with many important drug molecules, such as progesterone, the diffusion rate through a polydimethylsiloxane membrane is very great, and it is often greater than the rate of clearance of the diffused drug from the outer surface of the capsule. In many instances this results in the rate limiting step being clearance of the drug from the exterior of the capsule, rather than diffusion through the capsule wall. Clearance rate within the body is difficult to control, as it is subject to frequent change, and this inherently defeats the objects of providing a drug delivery device which releases drug at a constant rate over prolonged time.

In my copending application, U.S. Ser. No. 42,786 filed June 2, 1970 and now U.S. Pat. No. 3,854,480, and assigned to the assignee of this invention, there is described a novel drug delivery device comprised of a drug dispersed in a solid matrix permeable to passage of the drug and surrounded by a membrane, also permeable to passage of the drug but at a lower rate than through the matrix. That device has proven itself capable of zero order drug release and represents a substantial improvement over previously proposed drug delivery devices. The drug release rate in these devices is controlled by using nonporous wall forming materials for releasing the drug, and the release rate for the drug is proportional to its diffusion coefficient in the wall and to the solubility of the drug in the wall. In making these drug delivery devices available to the art, these parameters are developed for each drug, and it has now been found that this can require a large number of wall forming materials for different drugs. This often adds considerable complexity to the design of drug delivery devices.

It is also known to the art to incorporate drug into certain types of liquid carriers, usually in microcapsule formulations, for example, as in U.S. Pat. No. 3,464,413. However, these microcapsules are not designed for the controlled release of drug for a prolonged period of time by using drug release rate controlling materials. The microcapsules are frequently crushable, and they merely function as drug carriers supplying their drug in bulk, and not in controlled amounts by rupture of the microcapsules. Therefore, these types of capsules are not suitable for releasing drug at a controlled rate for a prolonged period of time. One additional approach used is described in *Die Pharmaz. Ind*, Vol. 51, No. 6, pages 409 to 412, 1969. This approach consists of coating a drug with a coat that undergoes a loss of mechanical properties in the environment of use such as swelling to form random holes for release of drug therethrough over a certain concentration range. This procedure has limited use because it requires a different coat for each environmental pH and the release of drug is dependent on its solubility in the fluid of the environment. These limitations inherently prevent these devices from reaching practical application.

SUMMARY OF THE INVENTION

Accordingly, it is an object of this invention to provide a device for the administration of locally or systemically acting drugs to produce a physiologic or pharmacologic effect which device overcomes the aforesaid disadvantages associated with the prior art devices.

Still another object of the invention is to provide a device for releasing drug at a controlled rate for a prolonged period of time.

Yet still another object of this invention is to provide a device which can release drug at a rate which does not vary with time.

Still yet another object is to provide a reliable and easily used device for continuously administering controlled quantities of drug to the body or to drug receptor sites.

Yet still a further object of the invention is to provide drug delivery devices that maintain their physical and chemical integrity in the environment of use.

A further object of this invention is to provide a complete dosage regimen for a particular time period, the use of which requires intervention only for initiation and termination of the regimen.

In accomplishing these objects and advantages of this invention, one feature of the invention, in its broadest aspect resides in a novel drug delivery device comprising a wall enclosing a reservoir. The reservoir is comprised of a drug within a solid carrier permeable to the passage of the drug, as by diffusion, and having limited solubility for the drug. The wall surrounding the reservoir is comprised in at least a part of a microporous material containing in its pores a drug release rate controlling medium permeable to the passage of the drug, as by diffusion, but at a lower rate than through the solid carrier. The medium in the micropores of the wall is supplied with drug by passage of drug from the solid carrier. Drug entering the drug release rate controlling medium present in the microporous wall passes through the medium for administration to the body or to a drug receptor site. Since the permeability of the solid carrier to the drug is always higher than the permeability of the drug release rate controlling medium, the passage of drug through the medium in the micropores of the wall is the rate determining step for drug release from the drug delivery device.

Other objects, features, and advantages of the invention will be apparent to those skilled in the art from the detailed description of the invention which follows, taken in conjunction with the drawings, and the accompanying claims.

BRIEF DESCRIPTION OF THE DRAWINGS

In the drawings, which are not drawn to scale, but rather are set forth to illustrate various embodiments of the invention, the drawings are as follows.

In the drawings and specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
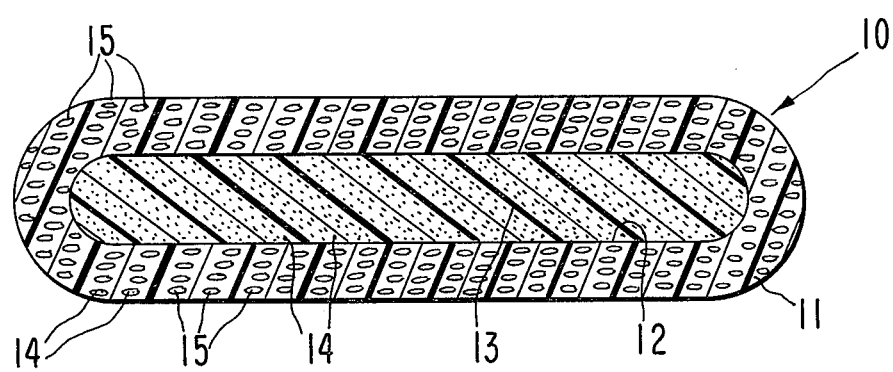
FIG. 1 is a perspective cross-sectional view of a drug delivery device of the invention depicting a wall surrounding a reservoir.
Figure 2:
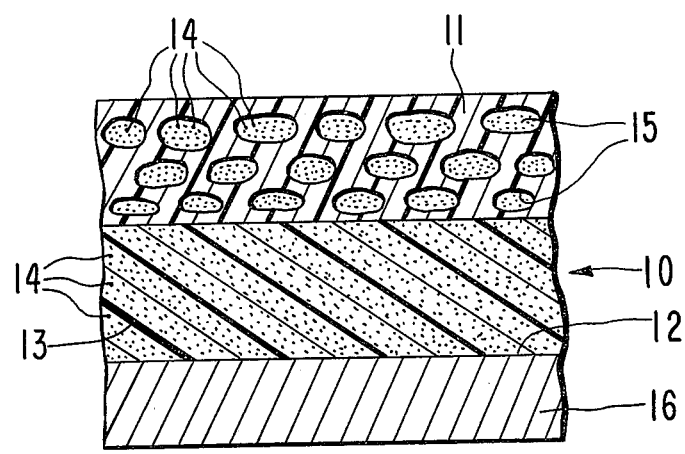
FIG. 2 is an enlarged cross-sectional view of a drug delivery device of the invention illustrating two different walls surrounding a reservoir containing a drug.

Turning now to the drawings in detail, which are examples of various drug delivery devices of the invention, and which examples are not to be construed as limiting, one embodiment of a novel drug delivery device is indicated in FIGS. 1 and 2 by the number 10. Drug delivery device 10 is comprised of a wall 11 surrounding a reservoir 12. Reservoir 12 is comprised of a drug carrier 13 as shown in both FIGS. 1 and 2 and contains a drug 14, or a mixture of drugs. Drug carrier 13 is a solid carrier, a description of which is presented later in the disclosure and it is permeable to the passage of drug 14, as by diffusion. Wall 11 is formed of a microporous material the micropores 15 of which contain a drug release rate controlling medium, not shown, permeable to the passage of drug, as by diffusion, or by convection,, or by a concurrent operation of both, but the rate of passage of the drug through the medium in the micropores is lower than the rate of passage of drug through the solid drug carrier. In operation, solid drug carrier 13 serves as a reservoir 12 by supplying dissolved drug 14 to the micropores 15 of wall 11 as drug molecules move through the carrier to bathe the inner surface of wall 11. Drug 14 present at the drug carrier/wall interface dissolves in and migrates through the medium, in the micropores 15 of wall 11, ultimately reaching the outer surface of wall 11. As drug 14 leaves drug carrier 13, undissolved drug present in reservoir 12 dissolves in solid carrier 13 to maintain a constant supply of dissolved drug in the carrier for continuously supplying drug at substantially the same rate to pores 15 of wall 11. The medium in pores 15 of wall 11 operates to effectively control the rate of release of drug throughout the useful period of drug release from the device. Thus, a zero order drug release rate can be obtained.

Wall 11 of drug delivery device 10 of FIGS. 1 and 2 is comprised as in FIG. 1 completely of a microporous material whose pores 15 are essentially filled with a medium permeable to the passage of drug 14; as by diffusion, or convection, or by both, or wall 11 is comprised as in FIG. 2 in at least a part of a microporous material whose pores 15 are essentially filled with a medium phase, not shown, permeable to the passage of drug 14 as by diffusion, or by convection, or by both. In FIG. 2, wall 16 comprising the remainder of device 10 is formed of a material impermeable to the passage of drug 14. The materials used to make wall 11 can have uniform pore properties across all its dimension, i.e., isotropic, or it can be of non-uniform microporous structures, i.e., anistropic, or it can be a material possessing both of these properties. When microporous wall 11 is made from the former material, that is, a material that is substantially uniformly porous, molecules of drug 14 dissolve in and diffuse through a liquid in pores 15 of wall 11 by the processes of diffusion, convection, or both. When wall 11 is made from the latter material, that is a material having non-uniform microporous properties, molecules of drug 14 diffuse through a liquid phase, not shown, present in the pores of varying sizes, for example, by diffusion, or by convection, or by both. When wall 11 is made from a material having both of these properties, drug 14 can be released from device 10 through medium contained in wall 11 by a concurrent operation of both of these mechanisms. In the specification, the premeation mechanism of drug release through the drug release rate controlling medium is generically described as "by diffusion" for both types of microporous materials used to fabricate wall 11. The permeability of the medium in the pores of wall 11 to the diffusion of drug 14 is lower than the permeability of solid drug carrier 13 to the diffusion of drug 14 and passage through the medium thus acts as the rate limiting step for drug release from device 10.

Figure 3:
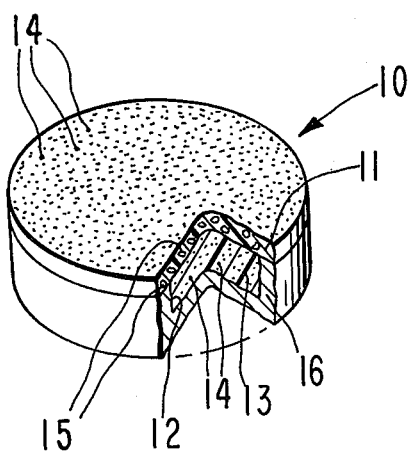
FIG. 3 is a schematic illustration of a drug delivery device shaped as a peroral tablet prepared according to the invention.

FIG. 3 represents a schematic drawing of a pill or tablet peroral drug delivery device 10 of the invention. This device 10 is comprised in at least a part of a wall 11 formed of a microporous material whose pores contain a liquid permeable to the passage of drug, as by diffusion, and it is also comprised in the remaining part of a wall 16 formed of a non-porous material, impermeable to the passage of drug. Wall 11 and wall 16 are made of essentially non-swellable materials and they enclose a reservoir 12 (shown in opened section) containing drug 14 in solid drug carrier 13. Carrier 13 is fabricated of a soidified material that remains in reservoir 12 during drug release and is permeable to the passage of drug, but the rate of passage of drug is higher in it than is the rate of passage of drug through the liquid in pores 15 of wall 11 so that drug release by the medium in the pores 15 of wall 11 is the drug release rate controlling step for releasing drug from the drug delivery device. The pill or tablet drug delivery devices are suitable for oral administration for continuously metering the flow of an effective amount of drug over a prolonged period of time to the gastrointestinal tract.

Figure 4:
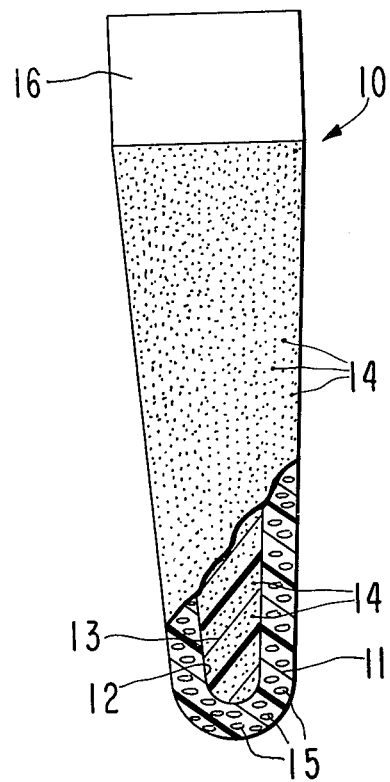
FIG. 4 is a side, fragmentary view depicting an anal drug delivery device of the invention for releasing drug in a body orifice.

FIG. 4 illustrates another drug delivery device of the invention. In FIG. 4, a drug delivery device 10 designed for administering drug within a body opening, the anal canal, not shown. Drug delivery device 10 of FIG. 4 is comprised of a microporous wall 11 surrounding a reservoir 12. Reservoir 12 is comprised of a drug carrier 13 containing drug 14. Drug carrier 13 is solid in nature. Carrier 13 is chemically distinct from the drug and it is permeable, as by diffusion, to the passage of drug 14, which has limited solubility therein. Wall 11 is made of microporous materials that can be visualized as a plurality of spongelike fused particles which provide a supporting structure having therethrough a dispersion of microscopic sized interconnecting voids or pores. Wall 11 can be isotropic, wherein the structure is homogeneous throughout the cross-section of the wall, or wall 11 can be anisotropic wherein the structure is non-homogenous throughout the cross-section of the wall. The materials forming wall 11 are insoluble in body fluids. Pores 15 of wall 11 contain a medium, not shown, permeable to the passage of drug 14, as by diffusion, and it releases drug from the device at a predetermined, controlled rate within the body. In this device, as with the device discussed above, drug released from carrier 13 is replenished by undissolved drug dissolving in solid carrier 13 to insure that drug is continuously available to wall 11. Also, in the device of FIG. 4, release of drug through the medium in pores 15 of wall 11 is the rate controlling step for release of drug from this device.

Figure 5:
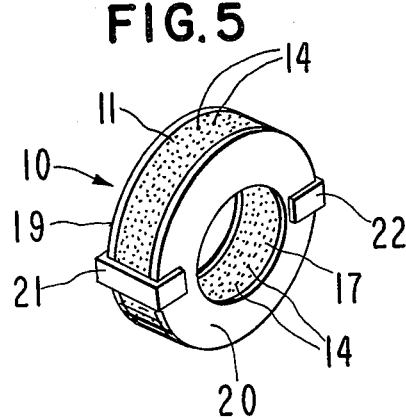
FIG. 5 is a schematic drawing showing a drug delivery implant that keeps its original mechanical shape and is fabricated in accordance with the invention.

In FIG. 5, there is illustrated a drug delivery device 10 for use as a depot implant. Device 10 is comprised of a wall 11 and a wall 17 surrounding a reservoir, not shown in this figure. Wall 11 and wall 17 are removably secured to the face of a pair of stainless steel washers 19 and 20 respectively. Two or more stainless steel U-shaped clips 21 and 22 are placed about washers 19 and 20 to clamp them tightly against wall 11 and wall 17 surrounding the reservoir. Wall 11 and wall 17 are formed from resilient materials and they will be compressed by clips 21 and 22. Wall 11 and wall 17 will tend to expand under the bias of clips 21 and 22 and hence form a tight seal with the periphery of wall 11 and wall 17.

In FIG. 5, wall 11 and wall 17 are both formed from a microporous material and wall 11 can be the same microporous material or it can be a different microporous material than the wall 17. Wall 11 and wall 17 are permeable to the passage of drug 14 as by diffusion through liquid in micropores in the walls, that is, by diffusive flow through a media contained therein. The diffusive media in the micropores of wall 11 can be the same as or it can be different than the diffusive media present in the micropores of wall 17. In actual operation, drug is released from a solid carrier which in this example is non-diffusible, remains in the carrier, is chemically distinct from the drug, and is in intimate contact with walls 11 and 17, by passing through the walls and the diffusive media in the pores of the walls at a controlled rate of release from drug delivery device 10. When the diffusive media in the pores of wall 11 and wall 17 are different, device 10 can release the same drug or a mixture of different drugs at different controlled rates of release for a prolonged period of time. As the drug leaves the carrier, undissolved drug in the reservoir dissolves in the solid carrier thereby continuously supplying the microporous walls with drug for administration or a zero order rate into a host to achieve a desired physiological or pharmacological benefit.

Figure 6:
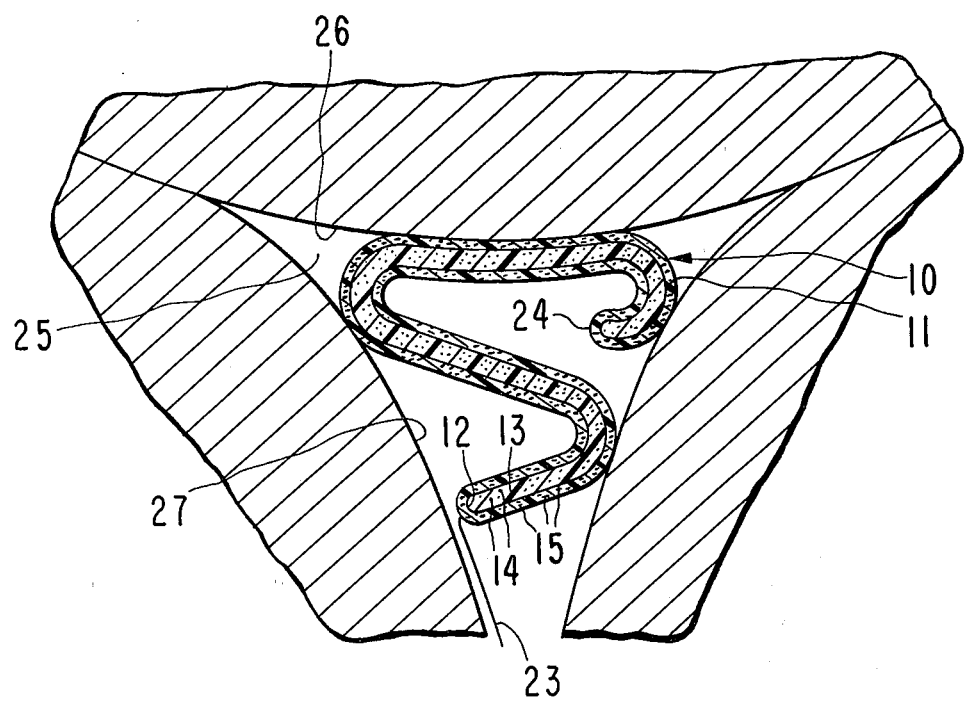
FIG. 6 is a frontal, fragmentary view of a uterine cavity showing a drug releasing intrauterine device positioned in the cavity.

In FIG. 6 there is graphically depicted an intrauterine contraceptive drug delivery device 10 prepared according to the spirit of the invention. Device 10 it will be seen consists of a sinuous form adapted to be located within the uterine cavity 25 and device 10 contacts the sides 27 as well as the fundus uteri 24 of uterus 25. Device 10 is capable of being substantially straightened by passing through a hollow instrument for positioning it in uterus 25. Device 10 has a memory 24 at its leading end which causes it to return to its original sinuous configuration in uterus 25 as it is positioned therein. Device 10 has a pair of nylon or surgical threads 23 attached to its trailing end for manually removing the device from the uterus.

Device 10 of FIG. 5 is comprised of a wall 11 housing a reservoir 12. Reservoir 12 is comprised of a solid carrier medium 13 containing a drug 14. The solid carrier confined in the reservoir serves several purposes for effectively releasing drug from the device. First, it is permeable to the passage of drug so that drug in the carrier can migrate to wall 11. Secondly, the carrier contacts and bathes the inner surface of wall 11 for facilitating drug transfer from the carrier to the wall so that drug molecules can dissolve in a diffusive medium in the microporous wall and migrate through it to the outer surface thereof. Thirdly, the solid carrier serves as a constant source of drug as it has a limited or varying degrees of solubility for drug or a mixture of drugs. The carrier is formulated to contain both dissolved and excess undissolved drug, and they can be homogeneously or heterogeneously dissolved and/or dispersed therein. Thus, the solid carrier is a constant source of drug because, as drug dissolves in the carrier and transfers from the carrier to the microporous wall, excess undissolved drug dissolves in the carrier to insure a constant and uniform supply of dissolved drug until essentially all of the drug has been released by the device. This mechanism of continually replenishing the drug enables the device to achieve a uniform release rate for the device throughout its use.

Wall 11 of the intrauterine contraceptive drug delivery device 10, is formed of a microporous drug release rate controlling material to continuously meter the flow of an effective amount of a drug from reservoir 12 for release within uterus 25. The rate of drug release through the microporous wall is through a diffusive media permeable to the passage of drug present in the micropores of wall 11, and this rate of drug release is lower than the passage of drug through and/or from the solid carrier, so that the former is the rate controlling step for drug release from the intrauterine contraceptive device. The depicted intrauterine drug delivery device is manufactured in a non-traumatising design for easy insertion into the uterine cavity. The device can be fabricated into assorted sizes, shapes, and thicknesses for adaptation to a wide variety of uteri.

Figure 7:
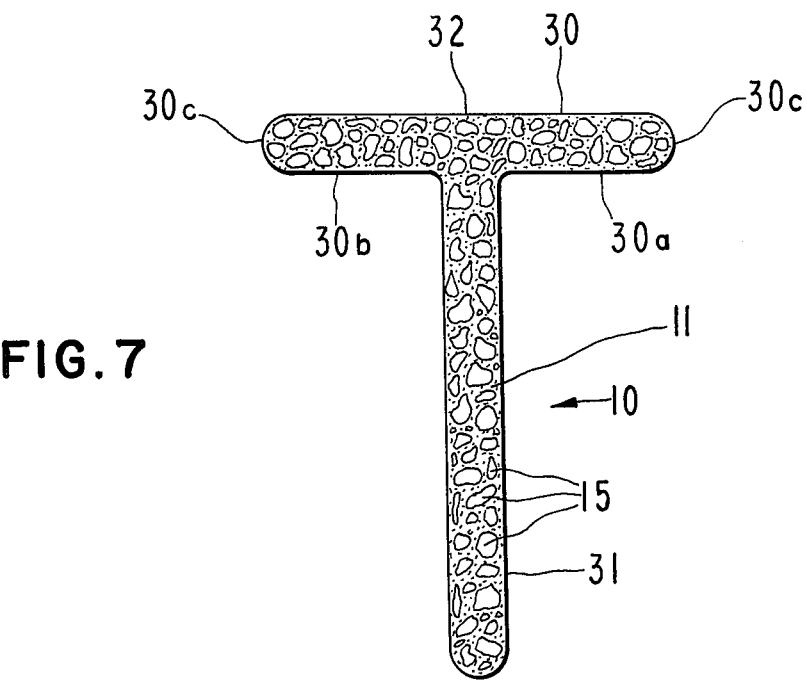
FIG. 7 is an opened view of another intrauterine device.
Figure 8:
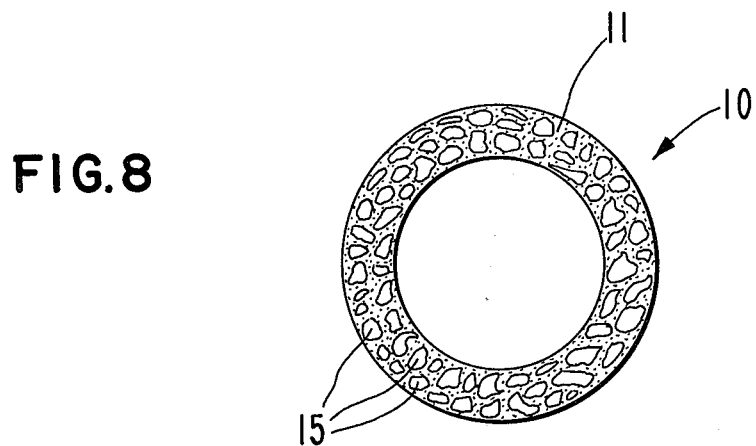
FIG. 8 is an illustration of a vaginal drug delivery device.

While the above FIGS. 1 through 6 and latter described FIGS. 7 and 8 are illustrative of various drug delivery devices that can be made according to the invention, it is to be understood that these drug delivery devices are not to be construed as limiting, as the drug delivery devices of the invention can take a wide variety of shapes, sizes and forms for administering the drug at controlled rates to different areas of the body or to different drug receptor sites. For example, the invention includes external and internal drug delivery devices such as skin patches, sublingual or buccal drug delivery devices, peroral devices, arterial devices, nasal and ear drug delivery devices, suture materials, plastic heart valves, Stan-Edwards heart valves, hip joints, non-thrombogenic hydrocephalus shunt, bone pins, pessaries, prosthesis, artificial glands, cervical rings, troches, intrauterine drug delivery devices of cylindrical, bullet, elliptical, circular, bulbous, loops, bows, or any other geometrical shape that readily lends itself to intrauterine placement such as Birnberg's Bow in U.S. Pat. No. 3,319,625; Comet in U.S. Pat. No. 3,256,878; Majzlin Spring in U.S. Pat. No. 3,397,691; Inhiband in U.S. Pat. No. 3,323,520; Bakunin in U.S. Pat. No. 3,405,711; Shamrock in U.S. Pat. No. 3,077,879; the ring with tail; Ota ring, and the like. In each instance, all of the drug delivery devices made according to the invention have a reservoir comprised of a drug and a solid drug carrier permeable to the passage of drug as by diffusion. The reservoir is surrounded by a wall, at least a portion of which is comprised of a microporous material whose micropores are filled with a diffusive media which is permeable to the passage of drug as by diffusion. The drug rate of release through the media in the microporous wall is lower than the rate of passage through the carrier, so that the drug release rate through the media in the wall is the drug release rate controlling step. Also, all of the drug delivery devices are of appropriate known shapes and sizes for implantation, insertion or positioning in the desired body cavities or on tissues for administering of drug to the body or to a drug receptor site.

DETAILED DESCRIPTION OF THE INVENTION

In accordance with the practice of the present invention, it has now been found that the drug delivery device of the invention provides many important advantages over previously known drug delivery devices. One advantage of the device is the ease of construction of the drug delivery device by standard manufacturing techniques into devices of various sizes, shapes and forms for delivering drugs to a recipient. A more important advantage of the claimed drug delivery device is to provide a broad range of drug release rates by providing one or more devices having a reservoir, or more than one reservoir in a large multi-purpose device, wherein the reservoir contains a solid carrier or a mixture of solid carriers having limited solubility for a drug or a mixture of drugs and where the carrier simultaneously releases drug and dissolves replacement drug to maintain a constant supply of drug for release by the device.

Another important advantage of the invention resides in the drug delivery devices' ability to effectively control the rate of release of the drug from the device by providing a zero order ($dM_t/dt$ = constant) rate of drug release throughout the major portion of the drug release history. The drug time release pattern for the device of the invention is obtained by a selection of the drug release parameters, such as, the size of the pores on a microporous wall, the ratio of the size of the pores to the molecular size of the drug molecule, the thickness of the material forming the wall, the porosity of the wall, the nature of the media in the pores, the nature of the drug carrier in the reservoir, and the kind of drug contained therein.

The above advantages and objects are achieved by the unique construction and operation of the device and its ability to transfer drug to a recipient or to a drug receptor site. In construction, the device can be viewed as a single unit constructed device comprising two structures acting in concert for effective drug administration to a host. One structure pertains to a microporous wall comprising the device and formed of a microporous drug release rate controlling material having present in its pores a diffusive media permeable to the passage of drug and the other structure relates to a reservoir comprising a solid drug carrier phase formed of a material permeable to the passage of drug. The materials forming the microporous wall and the drug carrier phase comprising the device are chemically and structurally different within a single device and the rate of release of drug through the media contained in the pores of the wall is lower than the rate of passage of drug in the drug carrier phase.

These two structures, comprising the unit drug delivery device, operate to effectively transfer drug from the device by first transferring drug from the carrier to the microporous wall, and secondly, by transferring drug through the media in the pores of the wall to a drug recipient. The transfer of drug through the media in the microporous wall occur by solution and diffusion, and it is sometimes referred to as diffusive flow. It is referred to in the specification and accompanying claims as diffusion. In the diffusion process, the drug dissolves in a media or mixture of media in the micropores of the wall and then diffuses in the direction of lower chemical potential. At the second boundary equilibrium is again established. When the boundary conditions on both sides of the wall are maintained constant, a steady state flux of the drug will be established which can be described by Fick's Law of Diffusion. The rate of passage of drug through the media in the microporous wall material is generally dependent, in the case of diffusion, on the solubility of the drug in the media, as well as on the diffusion coefficient and on the size of the pores and the porosity and tortuosity of the material. This means that selection of appropriate materials for fabricating the wall will be dependent on the particular microporous wall, the media and the drug to be used. In the device of the invention when the radius of the micropores is at least 10 times larger than the molecular radius of the drug molecule, there is no interaction between the wall material and the drug molecule. In this case, the drug diffusion coefficient will be the same as drug diffusion coefficient through a stagnant layer of the diffusive media. When the radius of the micropores is reduced to about 2 or 3 times the molecular radius of the drug molecule, interaction between the wall structure and the drug molecule can occur and will result in a lowering of the drug diffusion coefficient as hereinafter described. When the ratio of the radius of the micropore to that of the drug molecule is significantly lower than 2 to 3, it can be considered to be a solution diffusive membrane. Thus, by choosing the microporous wall material, and the release rate controlling media in the pores, the rate of passage of drug through the media ensures that the release kinetics of the device are controlled by the release rate of drug through the media in the microporous wall. Thus, by choosing the micropores and its media wall, a zero order release of drug, or a time release pattern of drug to the body or drug receptor site can be achieved.

The materials suitable for fabricating the microporous wall of the device are generally those materials through which the drug can pass at a controlled rate of release by the process of diffusion or diffusive flow through a media present in the micropores of the wall. Such materials are referred to in this specification and the appended claims as "drug release rate controlling materials." Suitable materials for forming the wall are naturally occurring or synthetic materials, preferably materials that are biologically compatible with body fluids, tissues or organs, and essentially insoluble in body fluids with which the device will come in contact. Generally, the use of rapidly dissolving materials or materials highly soluble in body fluids is to be avoided since dissolution of the microporous wall of the device would affect the constancy of the drug release, as well as the capability of the system to remain in place for certain uses for prolonged periods of time.

Exemplary naturally occurring or synthetic materials suitable for fabricating the microporous wall are drug rate release controlling materials known to the art, that are often described as a plurality of spongelike fused particles which provide a supporting structure having therethrough microscopic sized interconnecting voids or pores. The rate controlling structures formed from the materials can be isotropic, wherein the structure is homogeneous throughout the cross-section of the matrix or membrane material, or it can be anisotropic wherein the structure is non-homogeneous. The rate controlling structures are commercially available and they can also be made by different art known methods, for example, etched nuclear track, leaching, polyelectrolytic processes, ion exchange polymer reactions, and by other techniques as described in *Synthetic Polymer Membranes*, by R. E. Kesting, Chapters 4 and 5, 1971, published by McGraw Hill, Inc. and in *Ultrafiltration, Chemical Reviews*, Vol. 18, pages 373 to 455, 1934. Generally, materials possessing from 5% to 95% pores and having a pore size of from about 10 angstroms to 100 microns can be suitably employed in the practice of this invention. Materials with pore sizes significantly below 10 angstroms can be considered imperforate molecular diffusion or homogeneous type membranes.

The pore structure further includes continuous pores, which pore is one that has an opening on both faces of the microporous wall connected therethrough. For example, substantially cylindrical channels or cavities of various regular or irregular shapes including conventional forms such as uniform straight, uniform curved-linear, uniform curved, dispersed straight continuous pores, randomly oriented continuous pores, hindered connected through pores, and like pores that defined a diffusional path for passage through the microporous wall. The diameter of the pores are easily ascertained by measuring the observed surface of the membrane under the electron microscope. The pore diameter also is calculated from a guantity of liquid flowing out using the following relation 1:

$$R = k \sqrt{\frac{Ql}{ptA} \epsilon}$$

where $R$ is the pore diameter in micron; $k$ is a constant determined for the system; $Q$ is the quantity of liquid flowing out in g; $l$ is the thickness in mil with the devices having a wall thickness of 1 mil to 60 mil; $p$ is the pressure in g/cm$^2$; $t$ is the flowing-out time; $A$ is the filtering area in cm$^2$; $\epsilon$ is the void ratio of volume void over total volume of void; porosity is N where N is a positive integral 5 to 95% according to the relation 2:

$$N \left[ 100 \times \left( 1 - \frac{\text{weight of microporous wall}}{\substack{\text{weight of microporous wall} \\ \text{of same size free of micropores}}} \right) \right];$$

$t$ is the tortuousity in the relation 3:

$$t = \frac{\text{diffusional path length}}{\text{microporous membrane thickness}}$$

which is easily ascertained from relation $l$ wherein Q is the measured time for a fluid to flow through the microporous membrane, with for the system as disclosed, is always greater than 1, usually 1–60; as in *Science*, Vol. 170, pages 1302 to 1305, 1970; *Nature*, Vol. 214, page 285, 1967; *Polymer Engineering and Science*, Vol. 11, pages 284 to 288, 1971.

Materials useful in forming the microporous rate controlling materials used in this invention include, but are not limited to, microporous polycarbonates comprised of linear polyesters of carbonic acid in which carbonate groups recurs in the polymer chain, by phosgenation of a dihydroxy aromatic such as bisphenol A; microporous poly(vinylchlorides); microporous polyamides such as polyhexamethylene adipamide; microporous modacrylic copolymers including those formed of poly(vinylchloride) 60% and acrylonitrite 40%, styrene-acrylic acid copolymers, and the like; porous polysulfones, such as those characterized by diphenylene sulfone groups in linear chains thereof; halogenated poly(vinylidene) fluoride; polychloroethers; acetal polymers; material having predetermined pores made by conventional manufacturing methods; and the like.

Additionally, other microporous materials suitable for the present purpose include poly(urethanes); poly(imides); poly (benzimidazoles); cellulose esters; cellulose triacetate; cellulose; collodion(cellulose nitrate with 11% nitrogen); regenerated proteins; cross-linked poly(vinylpyrrolidone); anisotropic permeable microporous membranes of ionically associated polyelectrolytes, the polymers formed by the coprecipitation of a polycation and a polyanion as described in U.S. Pats. No. 3,276,589; 3,541,005; 3,541,006; 3,546,142; derivatives of polystyrenee such as poly(sodium styrenesulfonate) and polyvinylbenzyltrimethylammonium chloride; and the like. A large number of copolymers can be formed by reacting various proportions of monomers from the aforesaid list of polymers to form microporous materials by solvent evaporation useful for preparing rate controlling microporous structures.

The diffusive medium present in the micropores suitable for use herein are media permeable to the passage of drug, and in which the drug has limited solubility. Additionally, the media are generally non-toxic, and they do not adversely effect the drug or the microporous wall. The diffusive medium, in one embodiment, is a liquid phase comprised of a solution, a colloidal solution, a suspension, or a sol, and the medium can be polar, semi-polar, or non-polar. In these diffusive mediums, the drug can have different degrees of permeability and of solubility, limited to achieve a controlled drug release rate.

By limited solubility is meant that drug is soluble in given amounts in the diffusive medium, that is, it comprises varying concentration of drug that can dissolve in the medium. These varying limited solubility concentrations of drug in the medium include solubilities such as, soluble, sparingly soluble, slightly soluble, very slightly soluble, and almost practically insoluble. Generally, on a weight basis at 25°C, the amount of drug dissolved in a medium that is termed limited solubility is about 1 part of drug to about 10 to 25 parts of medium, the amount of drug dissolved in a medium that is sparingly soluble for the drug is 1 part of drug to about 25 to 100 parts of medium, from 100 to 1000 parts of medium for 1 part of drug when the drug is slightly soluble in the medium, from 1000 to 10,000 parts of medium for 1 part of drug when the drug is very slightly soluble in the medium, and from 10,000 to 15,000 parts of medium for 1 part of drug in a medium that is almost practically insoluble for the drug. Hence, the term limited solubility comprises a range of solubility of drug in medium of 1 part of drug to about 10 to 15,000 parts of medium on a weight basis at 25°C. The above ranges are set forth to aid in defining the invention, and they should not be considered as limiting as other ranges at higher or lower temperatures are embraced within the above presentation are also included herein.

The diffusive medium suitable for the immersion purpose are those well known to the art such as water, silicon oil, castor oil, olive oil, mixed oils, emulsions of castor oil in non-aqueous solutions of pigskin gelatin, emulsions of gum arabic, condensation products of castor oil and ethylene oxide combining about 30 to 35 moles of ethylene oxide per mole of castor oil, emulsifying and suspending agents such as methyl cellulose mixed with water, gum tragacanth, polymeric sodium alginate, cross-linked poly(vinylpyrrolidone), insoluble, non-solid plasticizers, fatty acids; assorted waxes; and the like. Representative mediums are set forth in *Remington's Pharmaceutical Science*, pages 246 to 269 and 1338 to 1390, 1970, published by Mack Publishing Company, Easton, Pa.

The diffusive medium can be added to the microporous material by methods well known to the art, for example, by immersion of the material in a bath containing the diffusive medium to let the medium partially fill or fully saturate the micropores of the material. Another method for charging the micropores with a diffusive medium is to first add to the reservoir a diffusive medium, or a mixture of diffusive media so that the medium can flow from within the reservoir into the pores and remain therein to permit diffusive flow of later added drug. The diffusive medium, in another embodiment, can be added to the pores of the material forming the wall by locating the wall in a fluid environment, for example, by contacting the device with a body tissue, for example, the mucous membranes of the anus, mouth or vagina, that can make available its intracellular and/or extracellular body fluid for subsequent transfer into the micropores of the wall for functioning as a diffusive medium for the drug. Additionally, the drug delivery device can be positioned in a body fluid, for example, in the fluid present in the stomach of farm animals, the avian cloaca, and the like, for using the fluid contained therein, as above described, as a diffusive medium. In another embodiment, the pores can be filled with plasticizer by immersing the wall in a plasticizer solvent composition, and removing the solvent in vacuo after the filling of the pores.

The materials comprising the microporous wall and the medium in the pores are chemically and/or structurally different than the materials comprising the solid carrier. Both of the materials are permeable to the passage of drug but the rate of flow through the medium in the pores of the wall is lower than the rate through the solid carrier. Thus, the rate of passage of drug through the medium in the wall is the rate release controlling step for the device. Generally, for the practice of this invention, the ratio of the drug release rate through the drug carrier of the reservoir to the drug release rate through the medium in the wall should be from 100:1 to 2:1 and preferably from 10:1 to 2:1. Of course, the invention is not limited to these release rates as the invention comprises lower or higher release rates from the solid drug carrier and lower and higher rates through the medium in the wall with the release rate of the medium in the wall lower than the release rate of the solid drug carrier. Thus, the invention provides that devices comprised of a solid carrier with various media in the wall pores activated by diffusion, can give different dosages of a drug by varying the characteristics of the respective materials to give controlled administration of a drug, *Encyclopedia of Polymer Science and Technology*, Vol. 9, pages 794 to 807, 1968.

For the above discussed devices, that is, diffusion through a material in the pores, the transfer or rate of release of drug through the medium in the wall is at a lower rate than the rate of release of drug from the drug carrier of the reservoir for administration to the body or to a drug receptor site. Thus, the passage of the drug through the medium in the wall is the drug release rate controlling step for the drug delivery system. In addition, because the reservoir serves to transfer drug molecules to all areas of the microporous wall, the microporous wall of the drug delivery system housing the reservoir remains substantially at the thermodynamic activity corresponding to that of the drug until substantially all of the drug has been released from the reservoir. Ordinarily, one would expect drug migration from the reservoir to cease when sufficient drug has entered the microporous wall to establish an equilibrium; however, when the drug delivery system is in contact with body tissues or fluids, drug molecules are continuously removed from the outer surface of the microporous wall. For optimum results, the rate of release of the drug through the microporous wall should be less than the rate of clearance of migrated drug from the external surface of the device. This ensures that the drug administration rate is dependent on the rate of release of drug through the microporous wall which can be controlled, rather than upon clearance of drug from the device in vivo, which can vary. Thus, in contrast to previously proposed drug delivery devices, the rate of release of the drug from the device of the invention can remain essentially constant until the drug delivery device has substantially completed its useful function.

The term reservoir as used in the specification and the accompanying claims generally refers to a drug carrier or to a medium containing drug, that constantly bathes the inner surface of the drug release rate controlling microporous wall and supplies drug thereto. That is, the reservoir is comprised of a solid drug carrier material containing dissolved drug, and/or undissolved drug, and/or a mixture of both, and it is a material that is permeable to the passage of the drug as by diffusion. The drug carrier medium used for the purpose of the invention is a solid, and it can be inorganic or organic, and of naturally occurring or synthetic origin. Examples of solid carriers comprised within the term solid are, for example, gelatin; starches; carbohydrates; solid extracts: of Irish moss; ethylcellulose; cured polymers; silicone carbonate copolymers; hydrophilic polymers such as hydrophilic hydrogels of esters of acrylic acids; modified collagen; surface treated silicone rubbers; plasticized poly(vinylchloride); and the like. Further, for the purpose of this invention, the terms solid carrier and the examples thereof are deemed as functional equivalents and they can also be generically termed solid core. *Remington's Pharmaceutical Sciences*, pages 1627 to 1679, 1970, published by Mack Publishing Company, Easton, Pa.

The solid drug carrier medium comprising the reservoir, also has in addition to the properties described supra, limited solubility for contained drug or for a mixture of drugs. By limited solubility is meant that drug is soluble in given amounts in the solid carrier, that is, it comprises varying concentrations of drug dissolved in the carrier. Essentially, there is also an excess amount of undissolved drug present in the carrier. These varying limited solubility concentrations include solubilities such as soluble, sparingly soluble, slightly soluble, very slightly soluble, and almost practically insoluble. The ranges of the drug to the carrier is as set forth above. Presently, when desired to obtain a zero order rate of drug release, the drug incorporated in the solid carrier is sparingly soluble so as to return substantially the same thermodynamic activity of the drug throughout the release period. By sparingly soluble is meant, in terms of amount, that the fractional amount of drug dissolved in the carrier should be in the range of from 0.1% to 35% by weight of the total amount of drug to be delivered, such that particles of undissolved drug are present throughout most of the drug release period. The amount of undissolved drug incorporated in the reservoir will vary depending on the type of drug delivery device, the particular drug, the desired therapeutic effect, and the rate of release of desired drug from the reservoir. That is, there is no critical upper limit on the amount of undissolved drug incorporated in the reservoir, since it serves as a reserve source of drug for replacing released drug by dissolving in the carrier to make drug continually available from the carrier to the wall during the history of the device, or until the device is no longer used. The lower limit will depend on the activity of the particular drug and the time span of its release from the device. Generally, the amount of undissolved drug initially present in the reservoir will range from about 90% by weight to about 99.9% by weight, of the total amount of drug present in the reservoir, where in a presently preferred embodiment, the amount present in the reservoir is about 250 micrograms to 4000 milligrams. Of course, the reservoir can have smaller or larger amounts.

The rate of release of a drug, that is the permeability, through various diffusive materials in the pores of the wall or the stagnant rate controlling layer can be easily determined by those skilled in the art by standard procedures, as described in *Encyl. Polymer Science and Technology*, Vols. 5 and 9, pages 65 to 82 and 794 to 807, 1968; and the references cited therein; in *Membrane Science and Technology*, by James E. Flinn, pages 16 to 32, and 120 to 138, 1970 published by Plenum Press Inc., *Chemical Engineers Handbook*, pages 17–42 to 17–45, 1963 published by McGraw Hill Inc. One applicable method employs Fick's Law of Diffusion, wherein the flux of drug through a convection-free medium, for example, a liquid present in a porous membrane is given by the equation:

$$J = \frac{-\epsilon D}{\tau} \frac{dc}{dx}.$$

wherein
- J is the flux in gm/cm²sec.,
- $\epsilon$ is the porosity in cm³/cm³,
- Y is the tortuosity factor,
- D is the diffusion coefficient cm²/sec,
- $dc/d\chi$ is the drug concentration gradient across the barrier.

Thus, when the diffusion coefficient is assumed to be independent of concentration, and the concentration at the outside surface is negligibly small, the equation can be expressed as follows:

$$J = \frac{\epsilon D}{Y} \frac{C_s}{l}$$

wherein
- $C_s$ is the saturation solubility of the drug in the diffusive medium; and,
- l is the barrier thickness.

The diffusion coefficient D will be in the order of $2 \times 10^{-6}$ cm²sec⁻¹ when the drug has a small molecular diameter, for example, about 10A and the pore diameter of the microporous matrix is large in comparison with the molecular drug diameter, for example, at least greater by a factor of 10. However, when the pore diameter of the rate controlling membrane is reduced relative to that of the molecular drug diameter, to for example from 10 to about 3 times the molecular diameter, the diffusion coefficient D will decrease to values as low as $2 \times 10^{-8}$ cm²sec⁻¹. When the ratio of membrane pore diameter to molecular drug diameter significantly is below about 3, the membranes are considered to be homogeneous solution diffusion materials. Thus, by varying pore diameter or porosity of the microporous materials, substantial changes in drug release rate can be brought about while still using the same materials.

The solubility of a drug in a diffusive medium can be determined by various art known techniques. One method consists in preparing a solution of the given drug and ascertaining by analysis the amount of drug present in a definite quantity of the medium. A simple apparatus for this purpose consists of a test tube of medium size fastened upright in a water bath maintained at constant temperature. The medium and drug are placed in the tube and stirred by means of a motor driven rotating glass spiral. After a given period of stirring, a definite weight of the medium is analyzed and the stirring continued for an additional period of time. If the analysis shows no increase of dissolved substance after the second period of stirring, the results are taken as the degree of solubility of the drug in the medium. Numerous other methods are available for the determination of the degree of solubility of a drug in a liquid medium. Typical methods used for the measurement of solubility are chemical analysis, measurement of density, refractive index, electrical conductivity, and the like. Details of various methods for determining solubilities are described in United States Public Health Service Bulletin No. 67 of the Hygienic Laboratory; *Encyclopedia of Science and Technology*, Vol. 12, pages 542 to 556, 1971 McGraw-Hill, Inc.; *Encyclopaedic Dictionary of Physics*, Vol. 6, pages 545 to 557, 1962, Pergamon Press, Inc.; and the like.

The solubility of the drug in the solid carrier of a device broadly is determined by preparing a saturated solution of a given drug and ascertaining, by analysis, the amount present in a definite area of the carrier. For example, the solubility of the drug in the carrier is determined by first equilibrating the carrier material with a saturated solution of the drug at a known temperature, for example 37°C, or with a pure liquid drug, if the drug is a liquid at 37°C. Next, drug is desorbed from the saturated carrier material with a suitable solvent for the drug. The resultant solution for the drug then is analyzed by standard techniques such as ultraviolet, visible spectrophotometry, refractive index, polarography, electrical conductivity and the like, and calculating from the data the concentration, or solubility of the drug in the solid carrier.

The diffusion coefficient of a drug is broadly determined by measuring the rate a drug transfers from one chamber through a sintered glass filter of known pore size and thickness into another chamber and calculating from the obtained data the drug transfer rate. The method when used for a diffusive medium is carried out by adding to a first conical flask equipped with a ground glass stopper and a stirring bar, a measured amount of medium and simultaneously, the drug in the same medium is added to a second conical flask while keeping the level of the medium in the two flasks the same. Next, the flasks are stirred, and samples drawn at various time intervals for analysis. The measured rate of drug transport through the sintered glass filter, and the concentration difference of the drug in the two flasks is then calculated. These procedures are known to the art in *Proc. Roy. Sci. London, Ser. A*, Vol. 148, page 1935; *J. Pharm Sci.*, Vol. 55, pages 1224 to 1229, 1966; and reference cited therein. The diffusion coefficient of a drug in the solid carrier can also be experimentally determined by using the above aparatus or similar apparatus and procedures as described in *Diffusion in Solids, Liquids and Gasses*, by W. Jost, Chapter XI, pages 436 to 488, 1960, Revised Edition, Academic Press Inc., New York.

The rate of release of a drug through various solid carrier materials can easily be determined by those skilled in the art by standard procedures. In this manner, particular carrier materials for use as the device's drug reservoirs can be selected. Various techniques, such as the transmission method, the sorption desorption method, and the like, can be used as measures of permeability. One technique that has been found to be eminently well suited is to cast or hot press a film of the solid carrier to a thickness in the range of 2 to 60 mils. The solid film is used as a barrier between a rapidly stirred (e.g., 150 r.p.m.) saturated solution of the drug and a rapidly stirred solvent bath, both maintained at constant temperature (typically 37°C). Samples are periodically withdrawn from the solvent bath and analyzed for drug concentration. By plotting drug concentration in the solvent bath versus time, the permeability constant P of the solid carrier is determined by the Fick's First Law of Diffusion.

$$\text{Slope of plot} = \frac{Q_1 - Q_2}{t_1 - t_2} = P \frac{AC}{h}$$

wherein
- $Q_1$ = cumulative amount of drug in solvent in micrograms at $t_1$ $Q_2$ = cumulative amount of drug in solvent in micrograms at $t_2$
$t_1$ = elapsed time to first sample i.e. $Q_1$
$t_2$ = elapsed time to second sample i.e. $Q_2$
$A$ = area of carrier material in cm$^2$
$C$ = initial concentration of drug
$h$ = thickness of carrier in cm.
By determining the slope of the plot, i.e.

$$\frac{Q_1 - Q_2}{t_1 - t_2}$$

and solving the equation using the known or measured values of $A$, $C$, and $h$, the permeability $P$ constant in cm$^2$/time of the material for a given drug is readily determined. Procedures for determining the rate of drug release through the carriers can be easily used by following standard techniques known to the art as recorded in J. Pharm. Sci., Vol. 52, pages 1145 to 1149, 1963; ibid. Vol. 53, pages 798 to 802, 1964; ibid. Vol. 54, pages 1459 to 1464, 1965; ibid. Vol. 55, pages 840 to 843 and 1224 to 1239, 1966; Encyl. Polymer Sci. Technol., Vol. 5 and 9, pages 65 to 82 and 794 to 807, 1968; the references cited therein, and the like.

Using the procedures and formulas above described, one skilled in the art can design a drug delivery device according to the invention by ascertaining the properties of the diffusive medium present in the micropores of the wall and the properties of the carrier forming material and then fabricating a drug delivery device by selecting a solid carrier in which the drug is permeable at a higher rate than the permeability of the drug in the medium in the pores of the wall. As an example for employing the teachings of this invention, consider a device consisting of a solid carrier in the shape of a thin slab of total thickness $l'$ bounded on all sides by a microporous membrane whose permeability to drug has been determined as $J_m$g/cm$^2$ sec, wherein m refers to the diffusive media in the micropores. Let the total drug loading of the carrier material be represented by the expression $\phi_c$g/cm$^3$, while the concentration of drug dissolved in the carrier be some lesser value represented by the expression $C_c$g/cm$^3$ and let the drug diffusion coefficient in the carrier be $D_c$. Then, after a time L, a quantity of J.A.L. grams of drug where A is the area will leave the carrier, mainly from those parts of the solid carrier which are immediately adjacent to the microporous membrane, leaving a layer of carrier next to the microporous wall of l in. thickness which contains no dispersed drug. Since, it is known to those versed in the art that the maximum rate of movement of drug to the microporous wall after time L is given by the expression $D_c C_c/l$ inch, which in turn is given by the expression $D_c C_c/J_m L$ $\phi_c$. Thus, for constant drug release, it is necessary that $D_c C_c \phi_c/J_m L$ always be $>> J_m$, generally by a factor of at least 2, preferably 5 over the prolonged use of the drug delivery device, that is, $D_c C_c \phi_c/L >> (J_m)^2$. Carrier materials suitable for constant release devices, therefore, have high solubilities for the drug $C_c$ and contain a large excess of drug dispersed in the carrier $\phi_c$, with the drug diffusion coefficient $D_c$ in the carrier material as large as possible. Hence, a selection of medium and carrier perameters as hereinbefore described, results in the preparation of a drug delivery device according to the invention.

In the specification and the accompanying claims, the term, drug, broadly includes physiologically or pharmacologically active substances for producing a localized or systemic effect or effects in mammals including humans and primates; avians such as chicken and turkeys; valuable domestic household, sport or farm animals such as horses, dogs, cats, cattle, sheep and the like; or for administering to laboratory animals such as mice, monkeys, rats, guinea pigs; and the like. That is, the novel drug delivery device can be used for administering drugs that are physiologically or pharmacologically active at a point in near relation to the drug delivery device, or, for administering a systemically active drug which will produce a physiological or pharmacological response at a site remote from the point of application of the drug delivery device. The active drugs that can be administered by the drug delivery device of the invention include, without limitation: for example, drugs acting on the central nervous system such as, hypnotics and sedatives such as pentobarbital sodium, phenobarbital, enitabas, secobarbital, thiopental, etc.; heterocyclic hypnotics such as dioxopiperidines, and glutarimides; hypnotics and sedatives such as amides and ureas exemplified by diethylisovaleramide and α-bromoisovaleryl urea and the like; hypnotics and sedative alcohols such as carbomal, naphthoxyethanol, methylparaphenol and the like; and hypnotic and sedative urethans, disulfanes and the like; psychic energizers such as isocarboxazid, nialamide, phenelzine, imipramine, tranylcypromine, pargylene and the like; tranquilizers such as chloropromazine, promazine, fluphenazine reserpine, deserpidine, meprobamate, benzodiazepines such as chlordiazepoxide and the like; anticonvulsants such as primidone, diphenylhydantoin, ethotoin, pheneturide, ethosuximide and the like; muscle relaxants and anti-parkinson agents such as mephenesin, methocarbomal, trihexylphenidyl, biperiden, levo-dopa, also known as L-dopa and L-β-3-4-dihydroxyphenylalanine, and the like; analgesics such as morphine, codeine, meperidine, nalorphine and the like; anti-pyretics and anti-inflammatory agents such as aspirin, salicylamide, sodium salicylamide and the like; local anesthetics such as procaine, lidocaine, naepaine, piperocaine, tetracaine, dibucaine and the like; anti-spasmodics and antiulcer agents such as atropine, scopolamine, methscopolamine oxyphenonium, papaverine, prostaglandins such as PGE$_1$, PGE$_2$, PGF$_{1\alpha}$, PGF$_{2\alpha}$, PGA and the like; anti-microbials such as penicillin, tetracycline, oxytetracycline, chlorotetracycline, chloramphenicol, sulfonamides and the like; antimalarials, such as 4-aminoquinolines, 8-aminoquinolines and pyrimethamine; hormonal agents such as prednisolone, cortisone, cortisol and triamcinolone; androgenic steroids, for example, methyltestosterone, fluoximesterone and the like; estrogenic steroids, for example, 17β-estradiol and ethinyl estradiol; progestational steroids, for example 17α-hydroxyprogesterone acetate, 19-nor-progesterone norethindrone and the like; sympathomimetic drugs such as epinephrine, amphetamine, ephedrine, norephinephrine and the like; cardiovascular drugs, for example, procainamide, amyl nitrate, nitroglycerin, dipyridamole, sodium nitrate, mannitol nitrate and the like; diuretics, for example, chlorothiazide, flumethiazide and the like; antiparasitic agents such as bephenium hydroxynaphthoate and dichlorophen, dapsone and the like; neoplastic agents such as mechlorethamine, uracil mustard, 5-fluorouracil, 6-thioguanine, procarbazine and the like; hypoglycemic drugs such as insulins, protamine zinc insulin suspension, globin zinc insulin, isophane insulin suspension, and other art known extended insulin suspensions, sulfonylureas such as tolbutamide, acetohexamide, tolazamide, and chlorpropamide, the biguanides and the like; nutritional agents such as vitamins, essential amino acids, essential fats and the like; and other physiologically or pharmacologically active agents. Also, the drugs can be present as the pharmacologically acceptable derivatives, such as ethers, esters, amides, acetals, etc. that lend themselves to passage into the circulatory system. For highly water soluble drugs, it is preferable that the wall or the reservoir, or both be formed from a material that is substantially impermeable to water to essentially prevent dilution of the drug by absorption of body fluids into the device with an accompanying decrease in drug release rate. These derivatives can be prepared by art known techniques and then used in the practice of the invention. Of course, the drug derivative should be such as to convert to the active drug within the body through the action of body enzymes assisted transformations, pH, specific organ activities, and the like.

The amount of drug present in the reservoir, whether dissolved, partially dissolved or undissolved, is generally non-limited and it is an amount equal to or larger than the amount of a drug that on its release from the device is effective for bringing about the drug's physiological or pharmacological local or systemic effects. For example, the amount of drug present in the reservoir of a drug delivery device when the device is used for a period of time to achieve local systemic effect is for various drugs, such as 11-desmethoxyreserpine about 5 to 40 mg in the reservoir; for acetophenazine an amount in the reservoir of 100 to 200 mg; for methoxypromazine about 600 to 750 mg in the reservoir; for emcylamate a reservoir amount of 1.5 to 2.0 gm; for phenylglycodol a reservoir amount of 1.5 to 1.9 gm; about 160 to 250 mg of butabarbital in the reservoir; about 150 to 170 mg of chlorodiazepoxide; from 0.5 to 1.2 gm of methsuximide; from 0.7 to 1.9 gm of ethosuximide; from 20 to 40 mg of hydrolazine; about 50 to 100 mg of totazoline; and the like. Generally, the drug delivery devices made according to the invention can contain from about 250 nanograms to 50 grams of drug for releasing it at a controlled rate of from about 25 nanograms to about 25 grams of drug or larger amounts per day. Of course, other devices containing different amounts of drug for use for different time periods such as week, month and year are also readily made by the invention.

It will be appreciated by those versed in the art that the unique drug delivery device of this invention can provide for the programmed delivery of drug at a rate of delivery characterized by a zero order time dependence for prolonged period of time; and, that the device therefore lends itself to administering an effective amount of drug needed for a therapeutic effect while essentially avoiding the presence of excessive amount of drug at the needed biological site. By a prolonged period of time is meant, as used herein, periods that embrace the time needed for a fast acting drug to effect its end up to periods that embrace the continual, uninterrupted, repititious time of a long term drug delivery device. For example, the prolonged time can be one hour or more for drugs, like local anesthetics, analgesics, prostaglandins or the like, that are effective in nanogram and milligram amounts, or the like, to three years or longer for steriods released within the uterine cavity. Other examples include wherein the amount of drug in the reservoir can be 100 to 300 mg of thiopropzate for releasing 15 to 30 mg over a 24 hour period; 200 to 400 mg in the reservoir of phenyltoloxamine for a release of 150 to 200 mg per day; 100 to 200 mg of papaverine in the reservoir for a topical release 30 to 75 mg over a 24 hour period; 2.5 g to 4.0 g of mephenoxalone for a release of 1.0 to 1.5 g per day; 15 to 25 mg of tranylcypromane for a release of 10 to 15 mg as the standard dose; 1 to 2 gm of trimethadione present in the reservoir for a release adminstration of 0.5 to 1.0 g per day; prostaglandins for example $PGE_1$, $PGE_2$, $PGA_1$, $PGF_{2\alpha}$ in amounts of 0.5 mg to 10 mg for release of 1 ng to 100 ng and the like; for progestogen or progesterone the administration in the uterus of 10 to 200 µg per day for release for 1 year to 3 years as an antifertility agent in a mature, child-bearing woman; an oral device administering 300 mg to 600 mg per day of analgesic acetaminophen to a 60 to 70 kg adult male; and the like.

The drug delivery devices of the invention are easily fabricated by using standard techniques. For example, in one embodiment, the reservoir comprising the solid carrier and the drug is fabricated by standard techniques. For example, in one embodiment a pre-cured liquid polymer can be mixed with the drug in solid, semisolid, or liquid forms at the time of mixing, and then distributed therethrough by conventional methods, such as ballmilling, calendering, stirring, shaking, rollmilling, and the like, followed by curing to yield a solid carrier. Next, the solid carrier is coated by spraying, dipping, and the like with a material that forms the microporous wall. In another embodiment a prepolymer and the drug are mixed and then charged into a drug microporous release rate controlling material, cured into a solid, and sealed therein. In another embodiment solid drug particles and solid carrier particles are compressed into a carrier and a microporous wall charged thereto to form a novel drug delivery device.

In another embodiment a liquid, pre-cured material and the drug are mixed charged into and cured in a highly permeable tube that is positioned within a microporous release rate controlling material. Alternatively, the tube can be coated with the microporous release rate material, or a microporous prepolymer can be cast around the tube and finally cured into a microporous drug release rate controlling material. The wall material forming the device and having the reservoir contained therein can be formed to a given drug design by molding, casting, pressing, extruding, drawing, rotational molding, compression and transfer molding, or like standard processes of manufacture. Also, depending on the material used to form the wall, a monomers may be cured at this stage of manufacture. The ability to design and shape the wall into tubes, rods, discs, films, rings and other highly reproducible shapes of controllable composition, readily results in fabrication of drug delivery devices with controlled characteristics and thus overcomes a significant disadvantage of previously described devices. Other standard procedures, as described in *Modern Plastics Encyclopedia*, Vol. 46, pages 62 to 70, 1969, well known to those skilled in the art can be used to fabricate the drug delivery device of the invention.

The following examples are merely illustrative of the present invention and they should not be considered as limiting the scope of the invention in any way, as these examples and other equivalents thereof will become apparent to those versed in the art in the light of the present disclosure, drawings and the accompanying claims.

EXAMPLE 1

A drug delivery implant device comprising a reservoir containing a drug in a solid carrier surrounded by a microporous drug release rate controlling wall is manufactured as follows: first, 25 parts by weight of milled crystals of progesterone are mixed with 70 parts by weight of polydimethylsiloxane and 5 parts by weight of silicone oil and the mixture well stirred to insure a homogenous mixture. Next, 0.25 parts by weight of stannous octoate catalysts are added to the first mixture, and the second mixture and poured into an oblong mold. This is then cured for 30 minutes under ambient conditions. Then, a microporous cellulose acetate coating having pores with a diameter that permits the passage of steroids, is bonded around the exterior surface of the carrier. The carrier is about 100 $\mu$m thick, has a tortuosity of 3, a porosity of 0.175, a D of $2 \times 10^{-6}$ cm$^2$sec$^{-1}$ to give a release rate of 0.5 $\mu$g/cm$^2$hr.

EXAMPLE 2

Following the procedure set forth in Example 1, a drug reservoir comprised of a solid carrier containing poly(vinyl pyrrolidone) having dispersed therein progesterone is housed within a microporous, continuous pathed pored cellulose diacetate wall prepared by generally following the example. The drug is permeable in the carrier and in a medium confined in the pores but the rate of passage is lower for the medium so that it controls the release of drug from the device.

EXAMPLE 3

A drug delivery device suitable for use as a tampon is comprised of an insoluble, regenerated, cellulose diacetate wall having an average pore size of 24 angstrom and shaped as an elongated cylinder defining a discrete reservoir. The reservoir is formed by making hydrocortisone in a solid carrier. The carrier is prepared by incorporating hydrocortisone in a solid carrier formed by polymerizing two equivalents of methylene bisisocyanate, one equivalent of 3,000 molecular weight polyether triol and one equivalent of 1,4-butanediol, and curing at 100°C for 60 minutes. The solid carrier is coated with the microporous membrane for having its continuous pores subsequently charged with a release rate controlling medium permeable to the drug by diffusion to meter drug from the device. Positioning of the drug delivery device within the cavity results in the metering of hydrocortisone through the microporous wall to the environment at a controlled rate during the used period of the device.

EXAMPLE 4

A drug delivery device shaped like an elongated end-tapered tablet is manufactured by mixing polydimethylsiloxane with 5000 micrograms of hydrocortisone alcohol. After uniformly mixing the ingredients with unvulcanized silicone rubbery stannous octoate catalyst is added and the mixture cured in a mold at room temperature. Then, a cellulose acetate membrane is bonded around the external face surface of the cured, solid carrier. The microporous wall is characterized by a porosity of 60%, and a pore size of 0.45 microns, and when it is inserted into a body, the device is effective to delivery controlled amounts of the drug.

EXAMPLES 5 TO 11

Other drug delivery devices made according to the procedure set forth in the disclosure and the previous examples include the following drug delivery devices containing 10 to 90% of drug in a carrier phase within a drug delivery device: comprising phenazocine hydrochloride in a solid carrier encased within microporous collodion; an intrauterine drug delivery device comprised of the drug progesterone, with the carrier in the reservoir comprised of ethylene vinyl acetate copolymer wherein the vinyl acetate is 33% of the copolymer and the microporous wall cellulose acetate, the use of ethylene vinyl acetate copolymer for drug delivery devices is the invention of applicants Higuchi and Hussain as disclosed and claimed in United States patent application Ser. No. 281,446, filed on Aug. 17, 1972; the device as just described wherein the carrier is formed from finely ground cross-linked poly(cis-1,4-polyisoprene); a drug delivery device comprising a non-thrombogenic hydrocephalus shunt consisting of a heparin in a solid carrier phase and surrounded with a wall of insoluble, microporous polyester; a drug delivery device for oral use shaped as a drug administering elastic rubber band wherein the reservoir contains a drug in a sparingly soluble solid carrier therefore surrounded with a microporous isotropic wall; a drug delivery device designed as a Stan-Edwards heart valve comprising a high density microporous anisotropic wall around a solid drug reservoir; and, a drug delivery device manufactured as a suture comprising a microporous wall formed by the coprecipitation of a polycation and a polyanion tightly encapsulated around a reservoir of drug dispersed in a solid carrier.

EXAMPLE 12

A drug delivery implant shaped like a rounded disc is manufactured by mixing polydimethylsiloxane with 2500 micrograms of phenylglycodol. After mixing the ingredients with stannous octoate catalysts, the mixture is cured in a discshaped mold at 40°C. Then microporous polyhexamethylene adipamide is applied to the surface of the cured solid drug charged carrier. The microporous wall has a porosity of 60%, a pore diameter of 40 angstoms of continuous pores having a length unit greater than the length unit of the applied coat, with a tortuosity greater than 1. Next, the device is placed in a pressure vessel containing an emulsion of gum arabic and pressure applied to fill the diffusional path with a diffusive medium permeable to the passage of drug. When implanted, the implant releases to a mammalian host an effective amount of drug at a controlled rate for a prolonged time.

EXAMPLE 13

The procedure of Example 12 is repeated in this example; all conditions are as described except the pores have a diameter of 50 angstroms, the external microporous wall is 10 mil thick, the continuous diffusional path is 10 mil, the tortuosity is 1, and the pores are charged with the condensation product of castor oil and ethylene oxide containing about 30 to 35 moles of ethylene oxide per mole of castor oil and permeable to the passage of drug by diffusion.

EXAMPLE 14

A microporous membrane of polyvinyl chloride with continuous diffusional conduits is prepared by leaching a film consisting of polyvinyl chloride and the pore forming agent poly[p(dimethylamino)styrene]. The film is cast in a joint solvent cyclohexanone and the solvent evaporated. Then, an aqueous acidic solution of hydrochloric acid is used to leach the pore former to yield microporous polyvinyl alcohol. The leaching is carried out at room temperature followed by washing with distilled water to remove the acid. The microporous membrane is then applied to the carrier of Example 12 to fully surround the solid drug loaded carrier.

EXAMPLE 15

To 30 parts of cellulose triacetate and 3 parts of cellulose diacetate is added a mixture of 60 parts methylene chloride, 28 parts ethanol, 2 parts dibutyl phthalate and 4 parts water and the mixture stirred to uniformity. Then, the solution is spread on a glass plate, dried at 25°C, subjected to a pressure of 0.5 atmosphere and dried at 100°C. The film is spread by doctor blade, to yield 100 mil thick film, with a porosity of 80%, a pore diameter of 45 angstrom, a diffusional path of 33 mils, and a tortuosity of 3. The film is applied to an intrauterine device shaped like a wave with the micropores charged with semi-emulsified corn oil, the carrier mixed vegetable oils charged with 250 mg of progesterone for a release rate of 0.75 $\mu g/cm^2 hr$ for release as a contraception to a fertile uterus of an adult child bearing woman.

EXAMPLE 16

The procedure of Example 1 is repeated in this example. In this example, an intrauterine device 10 is seen in FIG. 7 consisting of a transverse member 30 fixed to a longitudinal dependent member 31. Device 10 is formed of a microporous wall 11 having a plurality of micropores 15 surrounding a solid reservoir, not shown, containing a member selected from the group consisting of progestational and estrogenic antifertility steroids. Member 30 interconnects with dependent member 31 at lead end 32 with member 30 extended outwards in two directions to form a pair of arms 30a and 30b with each arm terminated in rounded ends 30c. Micropores 15 optionally can be charged with a diffusive liquid medium prior to uterine placement or micropores 15 can be charged in situ with uterine biological fluid. Devices prepared according to the instant example and by using techniques set forth in previous examples represent one more embodiment of intrauterine devices made available by the invention. In one embodiment, the device comprises a microporous wall having its pores charged with a drug release rate controlling liquid media with the wall surrounding an inner mass transfer conductor. The conductor contains dissolved and undissolved diffusible antifertility agent selected from the group of steroids consistinf of progestational, estrogenic steroids and mixtures thereof. The conductor in this embodiment contains from about 0.5 milligram to about 3,000 milligrams of steroid for releasing about 0.5 micrograms to 400 micrograms per day over a prolonged period of time. Steroid released by the device interfers with the reproductive process and prevents pregnancy by inducing physiological changes including decidua formation so the egg cannot implant, changes in the size of the glands often accompanied with atrophy, stroma and edematous uterine differences, and the like.

EXAMPLE 17

The procedure of Example 1 is repeated in this example with all conditions as previously set forth; except the continuous pore formed wall is regenerated cellulose xanthate of average pore diameter 24 anstroms, the film is 3 mil thick, the diffusional path is 6 mil, the tortuosity is 2 and the micropores are filled by immersion in mixed pharmaceutical acceptable diffusional oils.

EXAMPLE 18

The procedure of Example 16 is repeated in this example with all conditions as previously set forth. In this example, is seen FIG. 8, comprising device 10 defining a vaginal ring consisting of an external microporous wall 11 having a multiplicity of micropores 15 formed with continuous diffusional paths through wall 11. Wall 11 of device 10 surrounds a reservoir containing a solid drug carrier permeable to drug and charged with same. The carrier of device 10 is permeable to the passage of drug at a higher rate than through a liquid medium present in micropores 15. Micropores 15 can be prefilled with diffusive medium or charged in situ with vaginal fluid. The reservoir, not shown in this figure, can contain vaginal medications and antifertility agents selected from the group consisting of progestational and estrogenic steroids.

It will be understood to those versed in the art in the light of the present specification, drawings and accompanying claims that the invention makes available to the art both a novel and useful drug delivery device for administering a drug to produce a local or systemic physiologic or pharmacologic effect; as, the rate of rleease of drug administered from the device can be controlled to produce these effects, while simultaneously lessening or overcoming the undesirable effects frequently associated with the administration of drugs by prior art methods. Additionally, it will be understood the invention uses microporous wall materials that are distinct and different than homogenous walls free of micropores and semipermeable walls also free of micropores; and, the use of these microporous walls having their micropores charged with a rate controlling liquid permeable to the passage of drug enables the invention to effectively administer drugs to animals, including humans and the like. It will be further understood by those versed in the art that many different embodiments of this invention can be made without departing from the spirit and the scope of the invention. Accordingly, it is to be understood that the invention is not to be construed as limited, but it embraces all equivalents inherent therein.

I claim:

1. A drug delivery device for the continuous administration of a drug at a controlled rate to produce a beneficial result, said device comprising (a) a wall formed of a microporous material having a plurality of micropores with diffusional conduits through the wall, (b) a reservoir surrounded by the wall comprising a solid carrier containing dissolved and undissolved drug with the carrier permeable to the passage of the dissolved drug by diffusion, (c) a medium made of pharmaceutically acceptable release rate controlling material housed in the micropores with the medium permeable to the passage of drug by diffusion, and (d) wherein drug is metered at a controlled and continuous rate from the device by passage from the solid and through the medium for a prolonged period of time to produce the desired results.

2. The drug delivery device for the continuous administration of drug according to claim 1 wherein the rate of passage of drug through the medium is lower than the rate of passage of drug through the carrier so that release by the medium is release rate controlling for releasing drug from the device.

3. An intrauterine delivery device for continuously administering a uterine acceptable antifertility agent at a controlled rate, wherein the device is comprised of (a) a wall dimensioned for insertion and retention within the uterine cavity, the wall formed of a microporous material insoluble in uterine fluid and capable of maintaining its physical structure during its uterine use, and having a plurality of micropores with diffusional paths through the wall, (b) a reservoir surrounded by the wall, comprising a solid carrier containing dissolved and undissolved diffusible antifertility agent, said carrier permeable to the passage of agent and containing undissolved agent in an amount sufficient to replace dissolved agent in the carrier in an amount essentially equal to the amount of dissolved agent released from the device at a continuous and controlled rate for a prolonged period of time, (c) a liquid release rate controlling material housed in the micropores with the liquid permeable to agent by diffusion and nontoxic to the uterine environment, and (d) wherein agent is released from the device when positioned in the uterus by passage of agent from the carrier and through the liquid to yield the desired result.

4. The intrauterine device for continuously administering an agent according to claim 3 wherein the rate of passage of agent through the medium is lower than the rate of passage of agent through the carrier so that release by the medium is release rate controlling for releasing agent from the device.

5. An intrauterine device adapted for easy insertion and prolonged retention in a fertile uterus, the device consisting of a transverse wall formed of a microporous material having a plurality of pores with diffusional paths through said wall, a longitudinal wall dependent from the transverse wall and suitably united therewith, said longitudinal wall formed of a microporous material and having a plurality of pores with diffusional paths through said wall, a reservoir surrounded by the transverse or longitudinal wall, said reservoir comprising a solid carrier containing diffusible antifertility agent with the carrier permeable to the passage of agent by diffusion, a liquid release rate controlling material housed in said micropores, with the liquid permeable to agent by diffusion, and wherein the device releases agent when positioned in the uterus by passage of agent from the carrier and through the liquid to yield the desired result.

6. The intrauterine device adapted for easy insertion and prolonged retention according to claim 5 wherein the rate of passage of agent through the medium is lower than the rate of passage of agent through the carrier so that release by the medium is release rate controlling for releasing agent from the intrauterine device.

7. An artificial gland for dispensing a pharmaceutically acceptable agent having a physiological function essentially equivalent to a natural gland, wherein said gland is comprised of (a) a wall defining the gland and dimensionally adapted for insertion and placement within a biological environment to dispense said agent with the wall formed of an essentially nontoxic microporous material having a plurality of micropores with continuous diffusional paths, (b) a reservoir surrounded by the wall and containing a solid carrier permeable to an agent, (c) an agent present in the carrier in an amount sufficient for the device to meter agent therefrom at a continuous and controlled rate for a prolonged period of time (d) a liquid agent release rate controlling material permeable to the passage of agent by diffusion present in the micropores, (e) and wherein the gland releases agent in the environment of use by passage of agent from the carrier and through the liquid to the exterior of the gland to produce a useful physiological result.

8. The artificial gland for dispensing agent according to claim 7 wherein the rate of passage of agent through the medium is lower than the rate of passage of agent through the carrier so that release by the medium is release rate controlling for releasing agent from the gland.

9. A nasal delivery device for dispensing a drug within a nasal passage at a controlled rate wherein the nasal device is comprised of (a) a wall defining the device dimensioned for insertion and placement within a nasal passage, with the wall formed of a nasal acceptable microporous material, (b) a reservoir surrounded by the wall and comprised of a solid carrier permeable to drug and containing drug in an amount sufficient for the device to meter it at a continuous and controlled rate for a prolonged period of time from the device, (c) a liquid medium permeable to the passage of drug by diffusion charged in the micropores, and (d) wherein the device releases drug when in a nasal environment by passage of drug from the carrier and through the liquid to the exterior of the device to produce a useful result.

10. The nasal device for dispensing drug according to claim 9 wherein the rate of passage of agent through the medium is lower than the rate of passage of agent through the carrier so that release by the medium is release rate controlling for releasing drug from the nasal device.

11. An anal delivery device for continuously dispensing a drug within the anal canal at a controlled rate, wherein the device is comprised of (a) a body dimensioned for insertion within the anal canal, said body formed of a wall of microporous material having paths therethrough, (b) a reservoir in the body and surrounded by the wall, said reservoir containing a solid carrier and drug (c) a liquid drug release rate controlling material permeable to the passage of drug by diffusion in the micropores, and (d) wherein the device releases drug in the environment of use by passage of drug from the said device to the environment to produce a useful result.

12. The anal device for dispensing drug according to claim 11 wherein the rate of passage of drug through the liquid material is lower than the rate of passage of agent through the carrier so that release by the material is release rate controlling for releasing drug from the anal device.

13. A device for continuously administering a drug within the ear at a controlled rate, said device comprising (a) a body having a length in excess of its width and dimensioned for insertion within the ear, said body formed of a wall of microporous material and having drug release means, (b) a reservoir surrounded by the wall and consisting of a solid carrier charged with diffusible drug with the carrier permeable to drug, (c) a liquid release rate controlling material permeable to the passage of drug by diffusion in the micropores and (d) wherein the device when in the environment of use releases drug for a prolonged period of time.

14. The ear device for dispensing drug according to claim 13 wherein the rate of passage of drug through the liquid material is lower than the rate of passage of drug through the carrier so that release by the material is release rate controlling for releasing drug from the ear device.

15. A vaginal drug delivery device for continuously administering a vaginally acceptable drug at a controlled rate, wherein the device is comprised of (a) a wall defining the vagainal device dimensioned for insertion and retention within the vaginal cavity, with the wall formed of a vaginally acceptable microporous polymeric material having pores for movement of drug therethrough, (b) a reservoir formed by the inner surface of the wall and surrounded thereby, said reservoir comprised of a solid carrier permeable to the passage of diffusible drug with said reservoir containing drug in an amount sufficient to administer drug from the device at a continuous and controlled rate over a prolonged period of time, (c) a liquid release rate controlling material permeable to the passage of drug in said pore, and (d) wherein the device releases drug when positioned in the environment by passage of drug from the reservoir through the pores to the environment to produce a local or systemic beneficial result.

16. The vaginal drug delivery device for dispensing drug according to claim 15 wherein the rate of passage of drug through the liquid material is lower than the rate of passage of drug through the carrier so that release by the material is release rate controlling for releasing drug from the vaginal device.

17. A vaginal device according to claim 15 wherein the device is ring-shaped.

18. A buccal delivery device for continuously administering a buccally administrable pharmaceutically accpetable drug at a controlled rate, wherein the device is comprised of (a) a wall defining the device and adapted for drug release to a buccal substrate with said wall formed of a pharmaceutically acceptable microporous material, (b) a closed reservoir formed by the inner surface of the wall, said reservoir containing a solid carrier permeable to the passage of diffusible drug with carrier containing the drug in an amount sufficient to administer same from the device at a continuous and controlled rate for a prolonged period of time, (c) a liquid release rate controlling medium permeable to the passage of drug in the micropores, and (d) wherein the buccal drug is released from the device to the substrate by passage of the diffusible drug from the carrier and through the liquid medium in the micropores to yield a useful drug result.

19. The buccal delivery device for administering drug according to claim 18 wherein the rate of passage of drug through the medium is lower than the rate of passage of drug through the carrier so that release by the medium is release rate controlling for releasing drug from the buccal device.

20. A topical device for continuously administering a topically administrable drug at a controlled rate, wherein the device is comprised of (a) a wall defining a topical device and having a configuration corresponding to a biological topical substrate for administering drug thereto, with the wall formed of a pharmaceutically acceptable microporous polymeric material, (b) a reservoir surrounded by the wall and comprised of a solid drug carrier permeable to the passage of drug, (c) a liquid drug release rate controlling diffusion medium permeable to the passage of topically administrable drug in the micropores of said wall, and (d) wherein the drug is released from the device to the topical substrate at a continuous and controlled rate by passage of diffusible drug through the carrier and liquid from the device to produce a beneficial drug effect.

21. The topical device for administering drug according to claim 20 wherein the rate of passage of drug through the medium is lower than the rate of passage of drug through the carrier so that release by the medium is release rate controlling for releasing drug from the topical device.

22. An oral delivery device for continuously administering an orally acceptalbe beneficial drug, wherein said device is comprised of (a) a wall defining the oral device and formed of a pharmaceutically acceptable microporous material for releasing drug, (b) a reservoir surrounded by the wall and comprising a fixed, solid drug carrier having high diffusivity for drug, containing drug and permeable to the passage of oral, diffusible drug, (c) a liquid medium permeable to the passage of drug present in the micropores of the wall, and (d) wherein the drug is released from the device in the environment of use at a continuous and controlled rate by passage of drug from the device for a prolonged period of time.

23. The oral delivery device for administering drug according to claim 22 wherein the rate of passage of drug through the medium is lower than the rate of passage of drug through the carrier so that release by the medium is release rate controlling for releasing drug from the oral device.

24. An implant device for use in a biological environment for continuously adminsitering a beneficial implant releasable agent at a controlled rate, said implant comprising (a) a wall dimensioned for insertion and retention as a depot in a biological environment, with the wall formed of a biologically acceptable microporous material, insoluble in biological fluids and able to maintain its physical integrity during the agent release period, (b) a liquid release rate controlling medium permeable to the passage of agent housed in the micropores of the wall and maintained therein druing period of agent release from the implant, (c) a reservoir surrounded by the wall comprising a solid drug carrier, said carrier having high diffusivity for agent and containing dissolved and undissolved agent with the undissolved agent present in an amount sufficient to supply the wall with an amount essentially equivalent to the amount released by the implant over a prolonged period of time and (d) wherein when the implant is placed in the environment, diffusible agent is metered in an effective amount from the device to the environment to produce a local or systemic effect with the agent released at a controlled and continuous rate by passage through the carrier and medium over said prolonged period of time.

25. The implant device for administering agent according to claim 24 wherein the rate of passage of agent through the medium is lower than the rate of passage of agent through the carrier so that release by the medium is release rate controlling for releasing agent from the implant.

26. An intrauterine device for the administration of an antifertility agent at a controlled and continuous rate over a prolonged period of time, said device comprising, (a) a reservoir comprising both dissolved antifertility agent and undissolved replacement antifertility agent in a solid carrier permeable to the passage of the agent, said undissolved replacement antifertility agent in the solid carrier in an excess amount to continuously replenish and maintain dissolved antifertility agent substantially at its original amount in the solid carrier during the prolonged period of time, said reservoir surrounded by (b) a wall of a configuration which is substantially in the shape of a T, the wall made of a material insoluble in body fluid, and formed of a microporous material containing a diffusive medium permeable to the passage of the antifertility agent, with the permeability of the medium lower than the permeability of the carrier to the agent, (c) and wherein the device when placed in the uterus releases dissolved antifertility agent from the reservoir in an effective amount for contraception by metered passage through the release rate controlling medium, with released agent continuously replaced in the solid core by replacement agent simultaneously dissolving to substantially maintain the amount of dissolved agent in the solid carrier for release at a controlled and continuous rate over a prolonged period of time.

27. The intrauterine device for the administration of agent according to claim 26 wherein the rate of passage of agent through the medium is lower than the rate of passage of agent through the carrier so that release by the medium is release rate controlling for releasing agent from the device.

28. An intrauterine contraceptive device for administering a member selected from the group of antifertility agents consisting of progestational, estrogenic and mixtures thereof at a controlled and constant rate over a prolonged period of time up to three years comprising (a) a wall formed of a microporous material, the material insoluble in body fluid, and capable of substantially maintaining the device's shape throughout the prolonged period of time, said wall surrounding (b) a reservoir defined by the wall's inner surface with the reservoir comprising a solid carrier containing up to 4,000 milligrams of both dissolved and undissolved replacement agent, with the carrier permeable to the passage of the agent, with the undissolved replacement agent in the carrier present in an excess amount to continuously replenish and maintain a substantially constant supply of dissolved agent in the carrier during the prolonged period of time, (c) a medium present in the micropores and permeable to the passage of agent, with the permeability of the medium lower than the permeability of the carrier to the agent, (d) and wherein agent is administered from the device by releasing dissolved agent with such released agent replaced by undissolved agent to continuously maintain dissolved agent in the solid carrier for supplying it at substantially the same rate to the medium so that agent is metered at a controlled and substantially constant rate from the reservoir by passage through the medium over a prolonged period of time.

29. The intrauterine device for administering an agent according to claim 28 wherein the rate of passage of agent through the medium is lower than the rate of passage of agent through the carrier so that release by the medium is release rate controlling for releasing agent from the device.

30. A method for interfering with the reproductive process, wherein the method is comprised of continuously administering a contraceptive agent from an intrauterine device when placed in a uterine cavity, by the steps of: (a) inserting into the uterine cavity a device comprising a reservoir containing dissolved and undissolved replacement agent in a solid conductor permeable to the passage of the agent, the undissolved agent present in an amount in excess of its solubility in the conductor and in sufficient amount to maintain the dissolved agent during the prolonged period substantially equal to the amount of dissolved agent originally present in the conductor, the reservoir confined within an enveloping shaped wall made of a biologically acceptable material, insoluble in mammalian body fluid, and formed of a microporous material with the micropores charged with a diffusion liquid medium permeable to the passage of agent, (b) releasing said agent from said reservoir at a controlled, continuous, contraceptively effective rate by diffusional passage through said medium, and (c) continuously replacing the dissolved agent released from the reservoir by continuously dissolving replacement agent in the carrier to substantially maintain the amount of dissolved agent in the solid carrier at its original amount.

31. The method according to claim 30 wherein the rate of passage of agent through the medium is lower than the rate of passage of agent through the conductor so that release by the medium is release rate controlling for releasing agent from the device.

32. An intrauterine delivery device for the controlled and continuous administration of a uterine acceptable antifertility agent wherein the device is comprised of (a) a wall shaped and dimensioned for insertion and placement within the uterine cavity, the wall formed of a uterine acceptable microporous polymeric material insoluble in uterine fluid and capable of maintaining its physical integrity during its uterine use, and having micropores, (b) a reservoir surrounded by the wall, comprising a solid carrier containing dissolved and undissolved diffusible antifertility agent, said carrier permeable to the passage of agent and containing undissolved agent in an amount sufficient to replace dissolved agent in the carrier in an amount essentially equal to the amount of dissolved agent released from the device at a controlled and continuous rate for a prolonged period of time, and (c) wherein agent is released from the device when positioned in the uterus by passage of agent from the carrier and through the micropores to yield the desired result.

33. The intrauterine device according to claim 32 wherein the micropores are filled with a liquid release rate controlling medium in the environment of use.

34. The intrauterine device according to claim 32 wherein a diffusive medium is added to the micropores before the device is placed in the environment of use.

* * * * *